United States Patent
Guirguis

[19]

[11] Patent Number: 6,106,483
[45] Date of Patent: Aug. 22, 2000

[54] APPARATUS FOR OBTAINING A CYTOLOGY MONOLAYER

[75] Inventor: Raouf A. Guirguis, Rockville, Md.

[73] Assignee: LaMina, Inc., Herndon, Va.

[21] Appl. No.: 08/905,833

[22] Filed: Aug. 4, 1997

Related U.S. Application Data

[63] Continuation of application No. 08/474,894, Jun. 7, 1995, which is a continuation-in-part of application No. 07/680,896, Apr. 8, 1991, Pat. No. 5,139,031, which is a continuation-in-part of application No. 07/553,585, Jul. 18, 1990, Pat. No. 5,042,502, which is a continuation-in-part of application No. 07/411,041, Sep. 22, 1989, Pat. No. 4,953,561, which is a continuation-in-part of application No. 07/408,547, Sep. 18, 1989, Pat. No. 5,024,238, which is a continuation-in-part of application No. 07/308,763, Jan. 10, 1989, Pat. No. 4,961,432, which is a continuation-in-part of application No. 07/686,934, Apr. 18, 1991, Pat. No. 5,429,803.

[51] Int. Cl.$^7$ .................................................. A61B 1/06
[52] U.S. Cl. .............................................................. 600/562
[58] Field of Search .................................... 600/573, 562; 604/317, 318, 403, 404

[56] References Cited

U.S. PATENT DOCUMENTS

| | | |
|---|---|---|
| 536,552 | 3/1895 | Swift . |
| 3,722,502 | 3/1973 | Besuner et al. . |
| 3,774,455 | 11/1973 | Seidler . |
| 3,851,972 | 12/1974 | Smith et al. . |
| 4,040,791 | 8/1977 | Kuntz . |
| 4,170,056 | 10/1979 | Meyst et al. . |
| 4,395,493 | 7/1983 | Zahniser . |
| 4,435,507 | 3/1984 | Stenkvist . |
| 4,473,530 | 9/1984 | Villareal . |
| 4,557,274 | 12/1985 | Cawood . |
| 4,573,983 | 3/1986 | Annis . |
| 4,609,264 | 9/1986 | Podvin et al. . |
| 4,685,472 | 8/1987 | Muto . |
| 4,827,944 | 5/1989 | Nugent . |
| 4,960,130 | 10/1990 | Guirguis . |
| 5,022,411 | 6/1991 | Guirguis . |
| 5,038,793 | 8/1991 | Guirguis . |
| 5,077,012 | 12/1991 | Guirguis . |
| 5,143,627 | 9/1992 | Lapidus et al. . |

FOREIGN PATENT DOCUMENTS 0503128  9/1992  United Kingdom .

OTHER PUBLICATIONS

Jacalyn L. Papillo et al. B.S., CT (ASCP), Cell Recovery: ThinPrep Metod vs. Cytocentrifugatio.

Martha Hutchinson, Ph.D., M.D. et al., A Study of Cell Loss in the Conventional Pap Smear.

Katherine K. Mul et al., CT (ASCP), The ThinPrep Sample Preparation Process–A Matter of Reproducibility.

G.H. Green et al., Nuclepore Membrane Filter Techniques for Diagnostic Cytology of Urine and Other Body Fluids, Medical Laboratiory Technology, 30: 265–271 (1973).

Diagnostic Cytology, Nuclepore Corporation, 1–13.

The ThinPrep Processor and The CDS 1000 Cytology Work Station, Cytce Corporation, 1–21.

Goran Ocklind, Optically Eliminating The Visible Outlines Of Pores In Intact Polycarbonate (Nuclepore) Filters, ACTA Cytological, 31: 946–949 (1987).

Wartio Vaara et al., Nature, 238: 407–408 (1972).

James Robb, M.D. et al, Diagnostic Cytopthology, 14: 305–309 (1996).

James Linder, M.D., Arch Pathol Lab Med, 121: 282–286 (1997).

*Primary Examiner*—Max Hindenburg
*Attorney, Agent, or Firm*—Foley & Lardner

[57] ABSTRACT

The present invention is directed toward a cytology collection apparatus and a method for preparing a uniform monolayer of cells. The apparatus allows the rapid preparation from body fluids of a cytology monolayer with very few overlapping cells and with fewer contaminants than prior devices. The apparatus is in the form of an openable cell collection container which houses a filter for collection of cells when body fluid passes therethrough.

4 Claims, 9 Drawing Sheets

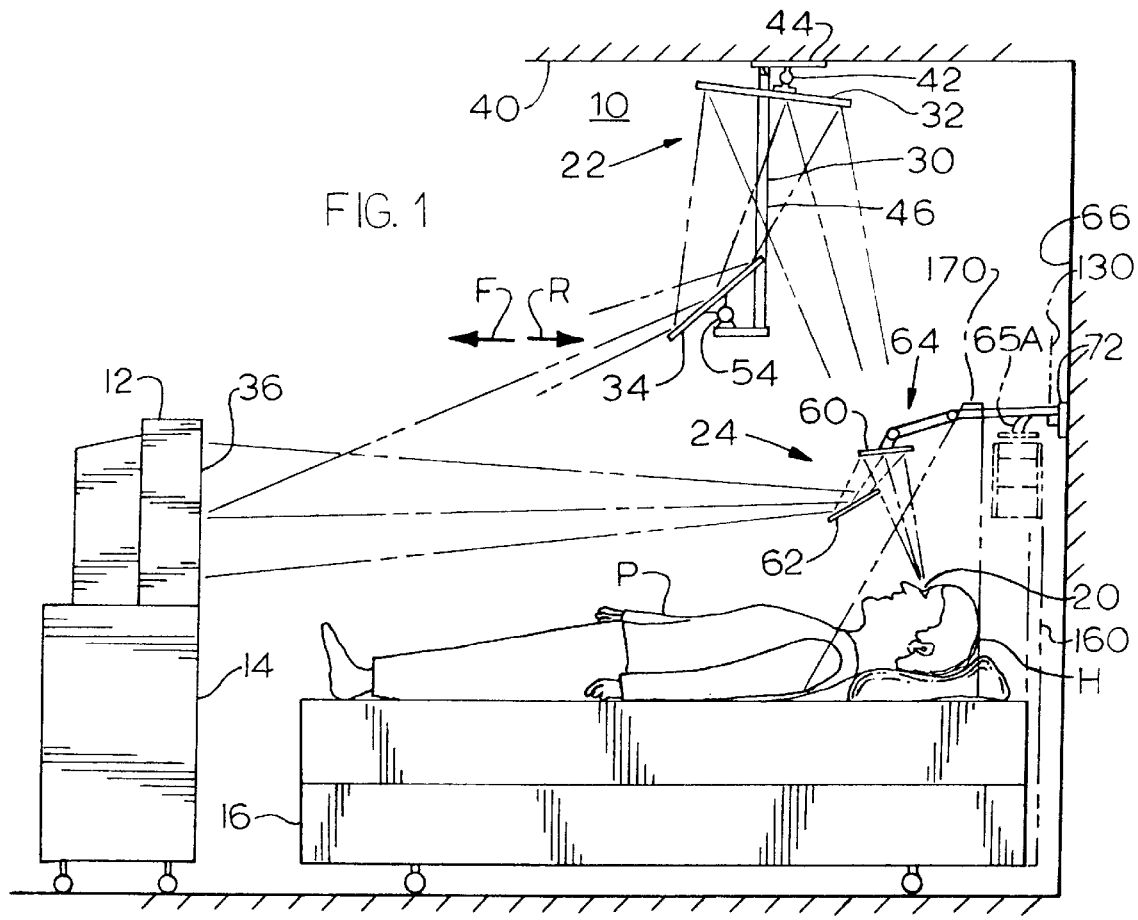
FIG. 1
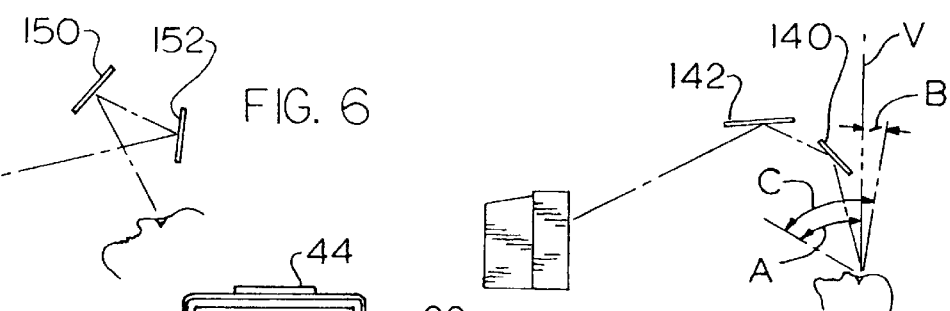
FIG. 6
FIG. 5
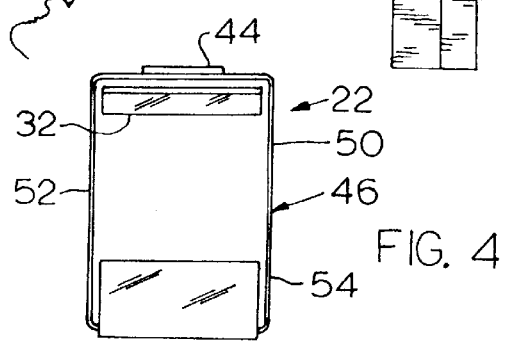
FIG. 4

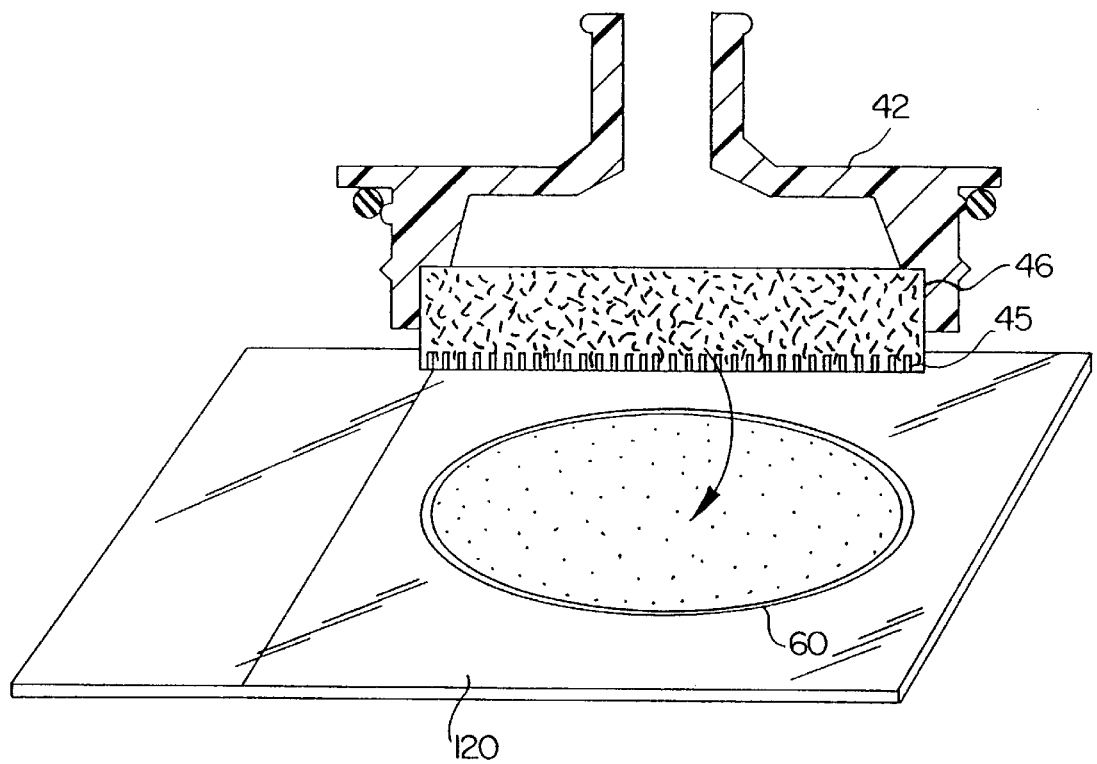
F I G. 10

APPARATUS FOR OBTAINING A CYTOLOGY MONOLAYER

CROSS-REFERENCE TO RELATED APPLICATIONS

This application is a continuation of application Ser. No. 08/474,894 filed Jun. 7, 1995 which application is now: pending, which is a continuation-in-part of U.S. application Ser. No. 07/680,896 filed on Apr. 8, 1991 now U.S. Pat. No. 5,139,031; which is a continuation-in-part of U.S. application Ser. No. 07/553,585 filed on Jul. 18, 1990 (now U.S. Pat. No. 5,042,502); which is a continuation-in-part of U.S. application Ser. No. 07/411,041 filed on Sep. 22, 1989 (now U.S. Pat. No. 4,953,561) and U.S. application Ser. No. 07/408,547 filed on Sep. 18, 1989 (now U.S. Pat. No. 5,024,238); which is a continuation-in-part of U.S. application Ser. No. 07/308,763 filed on Jan. 10, 1989 (now U.S. Pat. No. 4,961,432). The present application is also a continuation-in-part of U.S. application Ser. No. 07/686,934 filed on Apr. 18, 1991, now U.S. Pat. No. 5,429,803.

TECHNICAL FIELD OF THE INVENTION

The present invention is directed to an apparatus and method for collecting a uniform layer of cells from body fluids suitable for use in cytological protocols.

BACKGROUND OF THE INVENTION

Diagnostic cytology, particularly in the area of clinical pathology, bases diagnoses on a microscopic examination of cells and other biological samples. The accuracy of a diagnosis and the preparation of optimally interpretable specimen slides may depend both upon adequate patient sampling and on culture or slide preparation procedures.

Prompt processing of urine to obtain fresh cells traditionally has been recommended to ensure the accuracy of quantitative culture results, urinalysis and microscopy. Fresh cells tend to stick to a glass slide much better than cells from preserved urine, allowing for smoother cell spread onto the glass body. Delays in processing, negligent care in either inpatient or outpatient settings and lack of refrigeration may lead to non-optimal slide preparation. One known solution to the delay problem is the use of chemical preservatives with the urine. The presence of liquid preservatives, however, in the urine specimen raises the specific gravity of the specimen to unmeasurable levels and may limit the potential usefulness of the urine for various types of traditional quantitative analysis, such as slide microscopy.

A number of urine or other biological fluid specimen containers have been developed to allow liquid biological specimens to be tested without removing the lid of the urine or biological fluid container.

U.S. Pat. No. 2,953,132 discloses a parenteral solution bottle with an inwardly projecting tube and a rubber stopper and an associated dispenser bottle which is adapted to introduce medication into the parenteral solution bottle.

U.S. Pat. No. 3,066,671 discloses a disposable additive container provided with a cover formed with a shaft guiding sleeve. The shaft guiding sleeve receives an infusion holder and an additive container.

U.S. Pat. No. 3,608,550 discloses a transfer needle assembly for transferring fluid from a fluid source to a fluid collection container. The needle assembly includes a first cannula mounted on a support means which engages the collection container and is adapted to be connected at its forward end to the fluid source and at its rear end to the collection container. A second cannula is mounted on the support means and is adapted to be connected at its forward end to the fluid source and at its rear end to the atmosphere allowing fluid to be transferred from a fluid source to a collection container by atmospheric pressure when the volume within the collection container is sufficiently increased.

U.S. Pat. No. 3,904,482 discloses an apparatus and method for the collection, cultivation and identification of microorganisms obtained from bodily fluids. The apparatus includes an evacuated tube containing a culture medium, an inert gaseous atmosphere and a vent-cap assembly. The tube containing the culture medium is fitted with a stopper for introduction of bodily fluid by means of a cannula and, after growth of the organisms, transfer of the cultured medium is completed for subculturing or identification procedures.

U.S. Pat. No. 4,024,857 discloses a micro device for collecting blood from an individual or other blood source into a sampler cup. The cup has a removable vented truncated cone-shaped top with a capillary tube passing through a well formed in the top, proximate to the inside wall of the cup to deliver blood directly from the blood source to the cup.

U.S. Pat. No. 4,116,066 discloses a device for the collection of a liquid, such as urine, comprising an open ended urine collection container provided with a hollow cannula attached to its bottom. The cannula is slotted near its base, and serves as the conduit through which liquid may be transferred from the container to an evacuated tube. When the stopper of the evacuated tube is punctured by the cannula, the pressure differential causes liquid deposited in the container to be drawn through the slot into the hollow cannula and into the tube.

U.S. Pat. No. 4,300,404 describes a container which has a snap tight lid. The lid is provided with a cannula which extends into the lower end of the container and projects through the lid at its upper end so as to be able to pierce the stopper of an air-evacuated tubular container. The container is also provided with a depressed bottom to assure the maximum collection of fluids. The lid is provided with a recess to accommodate the air-evacuated tube.

None of the previously noted references solves the problem of transferring cells in a uniform layer to a slide for examination while at the same time preserving the fluid from which the cells were taken.

It should be noted that the process of transferring or collecting cells onto a slide or membrane is generally carried out by preserving or fixing the cytology specimen in the body fluid, secretions or smears.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives prior to transferring cells onto the slide or membrane for staining or examination. Desirable fixatives are alcohol and acetone fixatives.

The recovery (yield) as well as the quality of the cytology preparations from fresh body fluid specimens is superior as compared to routine cytology preparations requiring the use of preservatives. This is likely due to the fact that fresh cells stick better to glass and/or membranes than those preserved in alcohol or other preservatives.

SUMMARY OF THE INVENTION

The present invention relates to an apparatus and method for collecting a uniform layer of cells from urine or other biological fluid specimen in a cytology collection apparatus or assay module, which can be removably detached from a collection container for application to a slide. The collection container allows for the secondary collection of the biological fluid specimen along with the primary collection of cells. After collection of the cells in the cytology collection apparatus, the lid of the collection container may be replaced with a lid that seals the container and the biological fluid from which the cells were collected may be placed in a separate container (e.g., for storage or further assay). The separate container may be sealed by the patient or medical person handling the collection. The collection of the cells in the cytology collection apparatus allows a uniform cell slide to be obtained without contamination of the cells by preservatives, workers or outside materials. The transfer from collection container to the cytology collection apparatus may be carried out without pouring or pipetting the collected specimen.

The present invention is directed to a cell collection and distribution apparatus which can be disassembled to allow face to face transfer of cells from the device to a slide for microscope examination.

It is an object of the invention to provide a method for collecting a monolayer of cells which can be transferred to a slide and used for cytology.

It is another object of the invention to separately collect urine or other biological fluids from which cells have been extracted, without centrifugation, for use in diagnosis and testing. It is a further object of the invention to protect the fluid and the cell monolayer from outside contamination and to allow easy preservation and transport of the cells.

This invention is particularly useful for collecting cells for a pap smear.

The present invention is also directed to a cytology collection kit containing the cytology collection apparatus described above removably mounted to a fluid collection cup. The cytology collection kit may also include a means for inducing fluid flow through the cytology collection apparatus, preferably a syringe, removably mounted to the cytology collection apparatus.

According to another aspect of the present invention, the cytology collection kit may further comprise a debris filtering apparatus which is removably mounted to a cytology collection apparatus. The debris filtering apparatus removes debris and retains cells, which may then be expelled through the cytology collection apparatus to collect a monolayer of cells.

New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifact. These preparations have resulted in an even distribution of cells that have superior morphology, which has improved light microscopic visualization and has allowed for the use of image cytometry instruments.

The effectiveness of transferring the monolayer cells from the filter to the slide has proven to be very high without differential cell loss. Microscopic examination shows that the cell distribution was the same on the slide as on the filter.

This method of the present invention has many advantages for conventional cytology. The cells are in a predetermined area allowing for significant timesaving when screening the slide. Such problems as cells lying outside the coverslip or on the frosted end are eliminated. Because cells are lying in a single layer, they are almost always in a one focal plane when using a 10× objective—the objective most often used for the lower power screening of a slide. Even with a 40× objective, most cells are in focus. This eliminates frequent refocusing and saves time.

The minimal cell overlap achieved in this process ensures that all cells and cell groups can easily be examined with little chance for diagnostic cells to be obscured by clumps of overlapping cells or debris. Moreover, because the process takes place in the cytology laboratory, slide preparation and fixation are controlled by laboratory personnel and quality assurance is easily implemented.

The accompanying drawings show illustrative embodiments of the invention from which these and other of the objectives, novel features and advantages will be readily apparent.

DESCRIPTION OF THE DRAWINGS

FIG. 10 is a schematic cross sectional view of a second detachable portion, after removal from the cytology collection apparatus, showing the transfer of a monolayer of cells from the porous membrane onto a microscope slide.

DETAILED DESCRIPTION OF THE INVENTION

Figure 7:
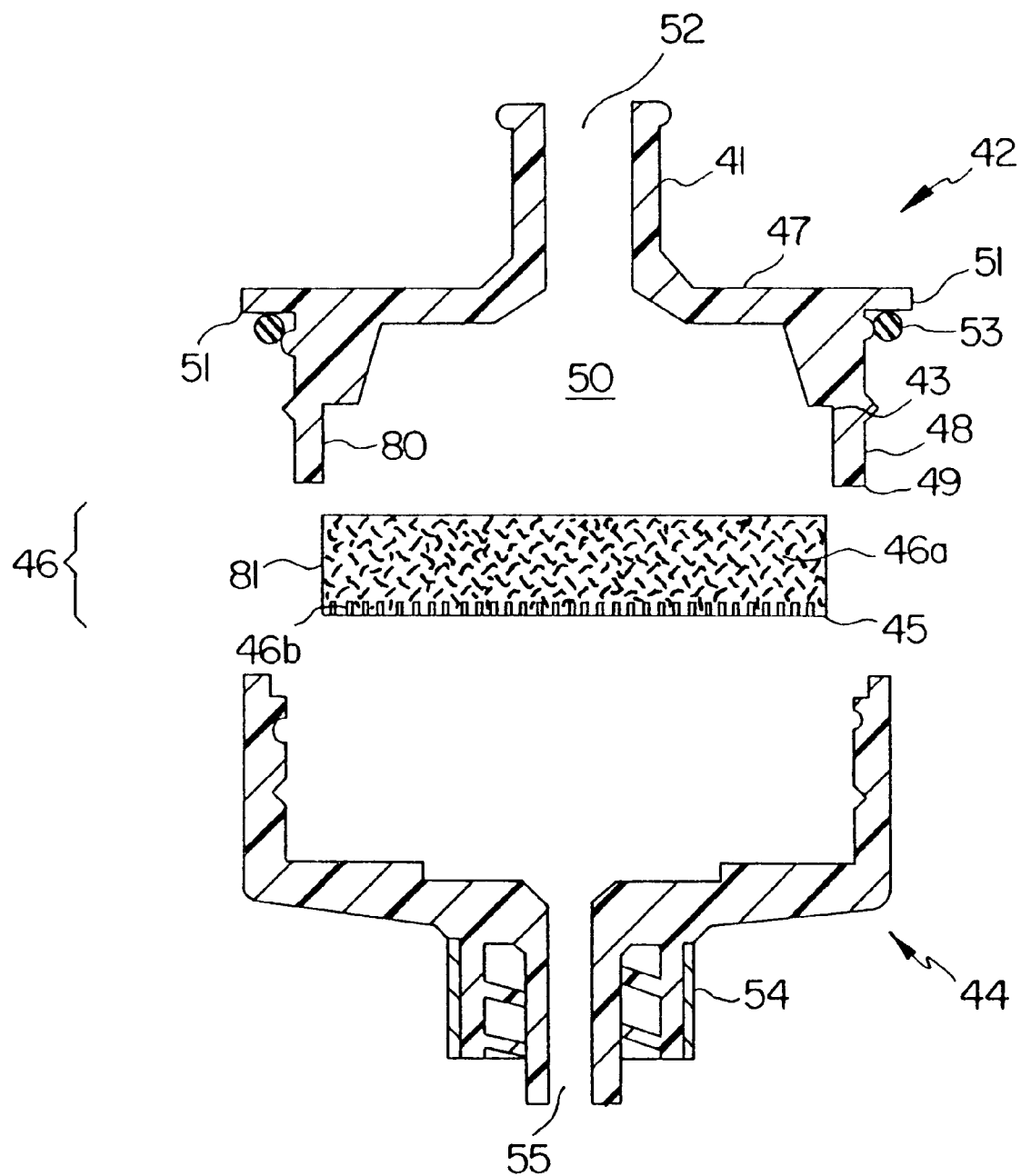
FIG. 7 is an exploded cross sectional schematic view of a cytology collection apparatus according to the present invention.

The present invention, an exemplary embodiment of which is shown in FIG. 7, includes an assay module or cytology collection apparatus 10, comprising first and second detachable portions 44, 42, having first and second ports 54, 41, respectively. The first and second detachable portions 44, 42 define a chamber 50 and the first and second ports 54, 41 define a fluid flow path through the chamber 50. A porous arrangement 46 having a collection site 45 adapted to collect cells may be positioned across the fluid flow path, the collection site 45 communicating with the first port 54. The porous arrangement 46 within the cytology collection apparatus 10 is preferably adapted to define a flow path having first and second branches, the first branch 60 extending through the collection site 45 and the second branch 61 bypassing the collection site 45. In a preferred embodiment, the invention includes a porous arrangement 46 having a first porous medium 46b, suitable for preventing the passage of cells therethrough, and a second porous medium 46a, suitable for removing particulate matter from the fluid. In a preferred embodiment, the porous arrangement 46 includes a first porous medium 46a and a second porous medium 46b, more preferably, a porous membrane 46b and a depth filter 46a wherein the depth filter communicates with the first port 54 through the porous membrane. In another embodiment, the depth filter 46a communicates with the first port 54 through a first branch of the flow path extending through the porous membrane 46b and communicates directly with the first port 54 through a second branch of the flow path.

The first port 54 may be configured as a connector and may be adapted to connect to a container, or may be configured as a needle or cannula 74 or the like. Second port 41 may be configured as a connector and may be adapted to connect to a syringe, or the like. The porous arrangement 46 may include a unitary structure having a first zone of density and pore size suitable to prevent the passage of cells therethrough and a second zone of density and pore size suitable for passing the fluid therethrough. The second zone may also remove particulate matter from the fluid. While the cytology collection apparatus 40 can be used for any biological fluid, it is particularly useful for preparing testing samples from urine and its associated cells for Pap smears.

It should be noted that various types of porous membrane can be used interchangeably with that of the present embodiment. While a polycarbonate membrane is especially suitable for use in the cytology collection apparatus of the present invention, other porous membranes are also suitable. One membrane that can be used for fluid screening is LEUCOSORB™, a leucocyte retention medium manufactured by Pall BioSupport Division of Pall Corporation. Other membranes manufactured and sold by the Pall Corporation are BIODYNE A™, an unmodified nylon with surface chemistry 50% amine and 50% carboxyl group which has an isoelectric point of pH 6.5; BIODYNE B™, a surface-modified nylon with surface chemistry characterized by a high density of strong cationic quaternary groups (the zeta potential is positive to pH>10); BIODYNE C™, a surface-modified nylon with surface chemistry characterized by a high density of anionic carboxyl groups (the zeta potential is negative to pH>3; and LOPRODYNE™, a low protein binding nylon 66 membrane with a tightly controlled microporous structure having high voids volume for rapid, efficient throughput of liquids and absolute retention of microparticles designed for cell separation and bacterial cell immunoassays.

In a preferred embodiment, the porous arrangement includes a porous polycarbonate membrane 46b, suitable for preventing the passage of cells therethrough. The porous arrangement may further include a depth filter 46a laminated to the porous polycarbonate membrane 46b. The depth filter 46a may be made of polypropylene or high density polyethylene POREX® porous plastics.

Figure 8:
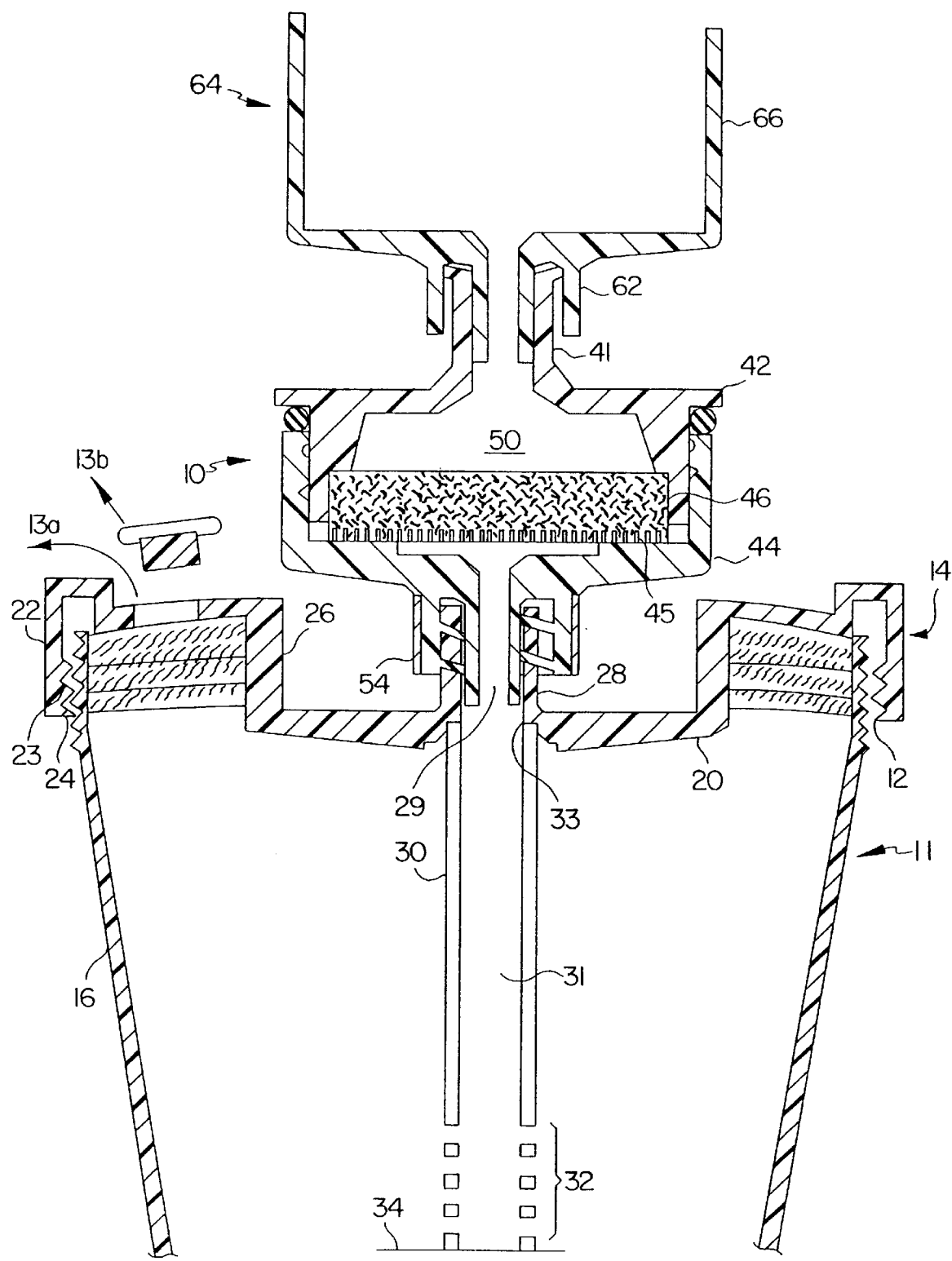
FIG. 8 is a cross sectional schematic view of a syringe and cytology collection apparatus mounted on a collection cup.

A preferred embodiment of the invention, shown in FIG. 8, includes an assay module or cytology collection apparatus 10 which may be mounted on a collection cup 11 in which urine or other biological fluids, such as blood, cerebrospinal fluid (CSF), bronchial lavage, sputum or fine needle aspirates may be collected. The collection cup 11 may be any container suitable for collection of body fluids. After fluid collection, the patient or supervising medical personnel places a lid 14 on the cup housing 16. The cup housing 16 is preferably provided with an external threaded surface 12. The lid 14 may include a vent hole 13a with an optional removable vent cap 13b. The vent hole 13a may also be used to introduce a brush or spatula into the cup containing physiological saline solution or preservative after brushing or scraping the body site to obtain the cytology specimen. Preferably, the lid has a body 20 which is molded with a downwardly directed cylindrical extended skirt or flange 22 which is threaded 24 on its inner surface 23 for screwing onto the external threaded surface 12 of the cup housing 16. The lid body 20 also defines a well 26 in which a threaded nipple 28 may be integrally molded. The nipple 28 is provided with a channel 29 or the like leading to a hollow tube 30 which is preferably separately secured to the other side of the lid body in a circular planar seat 33 with its lumen 31 being axially aligned with the channel 29 of the nipple 28. The tube 30 may have a series of perforations 32 and an open end 34 near the bottom of the collection cup 11 which allow different fluid layers as well as urinary sediments to be simultaneously tested when the urine or biological fluid is withdrawn from the cup.

Figure 2:
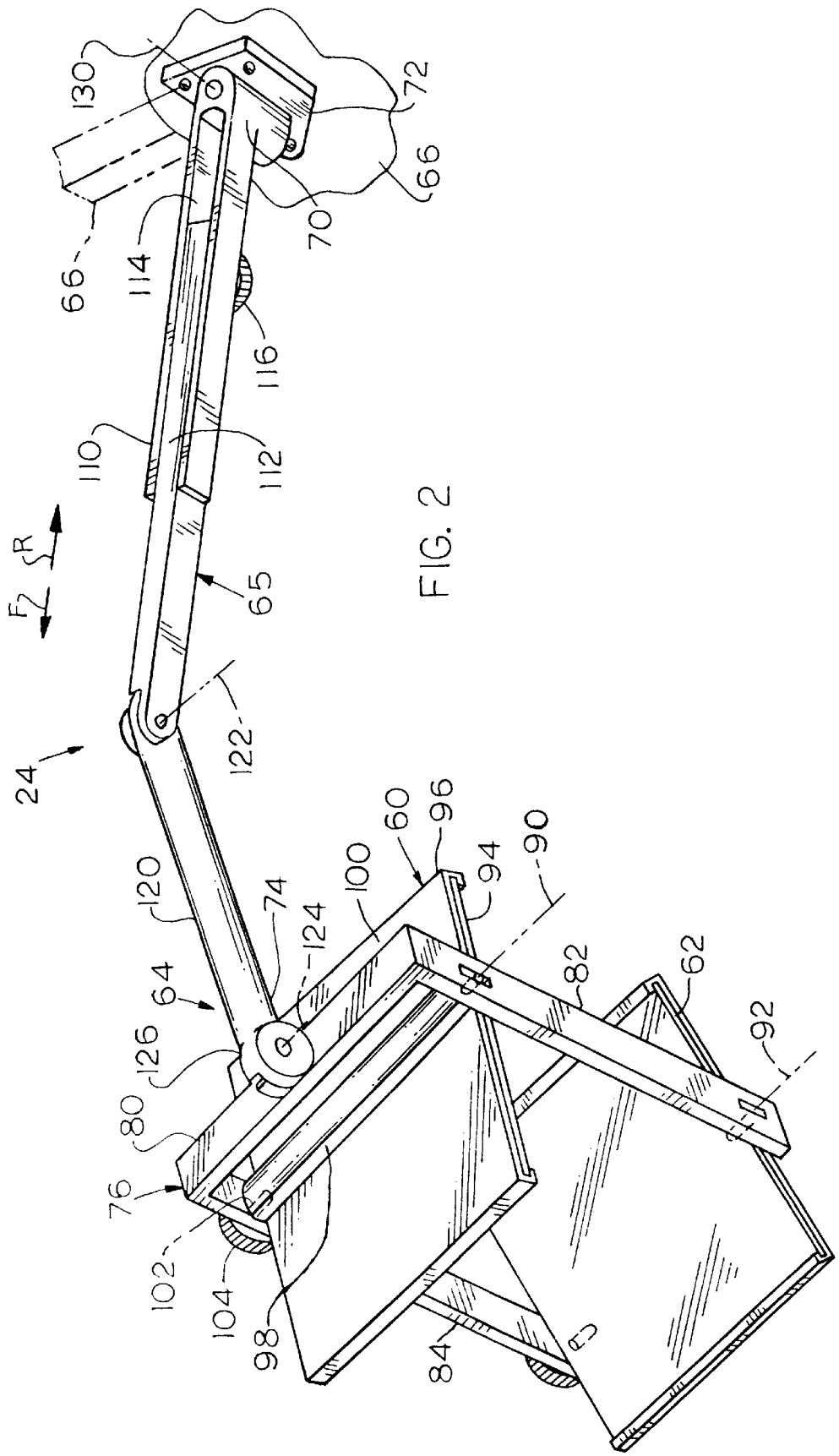
FIG. 2 is an exploded perspective view of a cytology collection apparatus according to the present invention.
Figure 3:
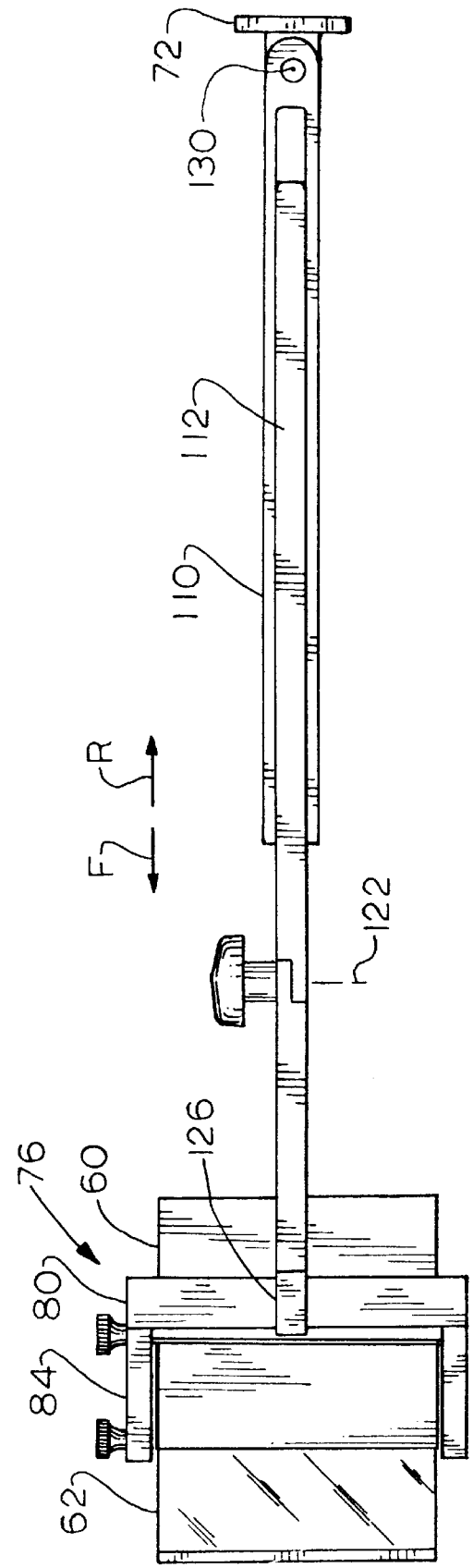
FIG. 3 is a perspective view of the porous arrangement according to the present invention, including first and second porous media.
Figure 1:
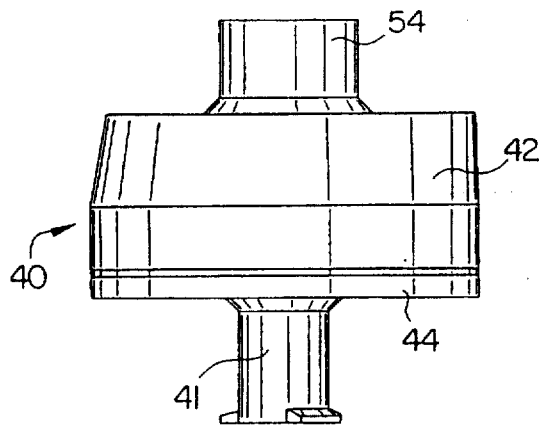
FIG. 1 is a perspective view of a cytology collection apparatus according to the present invention.
Figure 2:
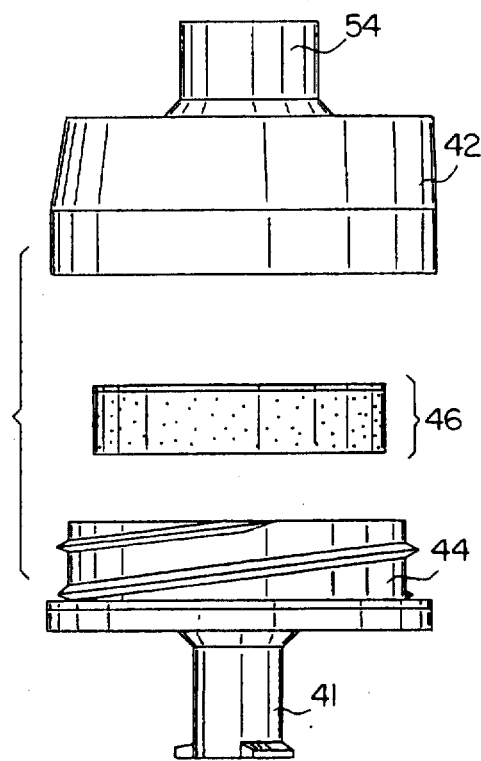
Figure 3:
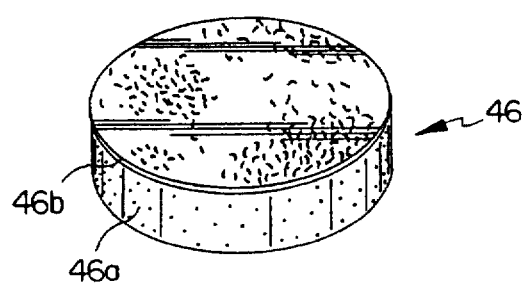

As shown in FIGS. 1, 2 and 7, the cytology collection apparatus 10 is preferably a two piece housing 40 with a first detachable portion 44 and a second detachable portion 42, although any housing providing access to the porous arrangement 46 is suitable. Preferably, a first porous medium 46b is mounted on a second porous medium 46a to form the porous arrangement 46. More preferably, a porous polycarbonate membrane 46b is laminated on filter member 46a to form the porous arrangement 46. The porous arrangement 46 may be mounted on an annular step or seat 43 formed in the interior cavity 50 of the second detachable portion 42.

The porous polycarbonate membrane 46b preferably has a pore size from about 0.22 microns to about 8 microns, more preferably from about 1 micron to about 6 microns, most preferably about 2 microns, which allows it to trap cells which are more than 3 microns in size. The polycarbonate membrane 46b, which may be mounted on the second porous medium 46a, is suitable to allow fluid flow to pass therethrough while preventing the passage of cells 60. The second porous medium 46a is suitable for passing fluid therethrough and may also be capable of removing particulate matter from the fluid. The pore size of the second porous medium 46a may range from about 5 microns to about 60 microns, preferably from about 15 microns to about 45 microns, most preferably about 35 microns.

As noted above, the second port 42 may be adapted to connect to a syringe 64, or the like. Exemplary connections include, but are not limited to a luer lock, a threaded luer lock, a friction connection, a tapered hose connection and a threaded connection.

Any means suitable for inducing the flow of fluid from a source container through the cytology collection apparatus may be used as part of the present invention. Exemplary fluid flow inducing means include, but are not limited to a syringe or pump type device. Syringe 64 has a barrel 66 and a piston (not shown) with assault piston head. In place of syringe 64, any suitable pump type device, such as an autovial spunglass filter manufactured by Genex Corporation, could be used. Also included in the scope of the present invention is the use of a flexible, collapsible container, such as a specimen container, which may be squeezed to force fluid through the cytology collection apparatus and into the syringe.

The cytology collection apparatus 10, as more clearly shown in FIGS. 1, 2, 7 and 8 may be mounted to syringe luer lock 62 and the nipple 28 of collection cup 11. The cytology collection apparatus 10 preferably includes an easily openable housing and may comprise a simple two-piece construction including a first detachable portion 44 and a second detachable portion 42. Preferably, the cytology collection apparatus 10 comprises a female detachable portion 44 screwed onto a male detachable portion 42. A skirt member 48 extends outward from base 47 and defines a cavity 50 and a flange 51 which holds O-ring 53. The cavity 50 communicates with the bore 52 of the port 41. The skirt 48 includes an annular step 43, which forms a seat for a porous arrangement 46. The inner surface 80 of the skirt 48 may be threaded. The porous arrangement 46 may comprise a polycarbonate membrane 46b laminated onto a disk shaped second porous medium 46a, which is preferably a depth filter. The second porous medium 46a may be provided with an outer cylindrical wall 81 having a threaded external surface, if such is desired, to screw into the step channel cut into skirt member 48 of the second detachable portion 42. The outer cylindrical wall 81 of the porous arrangement 46 may extend past the end wall 49 of skirt member 48. The area of the porous arrangement 46 which extends past skirt end wall 49 may act as a vent (low resistance to flow) to prevent piling up of cells on the surface 45 of the porous membrane 46b.

As noted, the second detachable portion 42 may be provided with a threaded nipple 41 having a throughgoing bore 52. The body of the second detachable portion 42 (planar base 47 and skirt 48) defines a frustro conical chamber or cavity 50 in which a step 43 is formed which serves as a seat for the porous arrangement 46. As previously noted, port 41 of the cytology collection apparatus 10 may be a threaded projection which is adapted to fit onto the luer lock 62 of a syringe 64, such as one manufactured by Becton Dickinson & Co.

Figure 9:
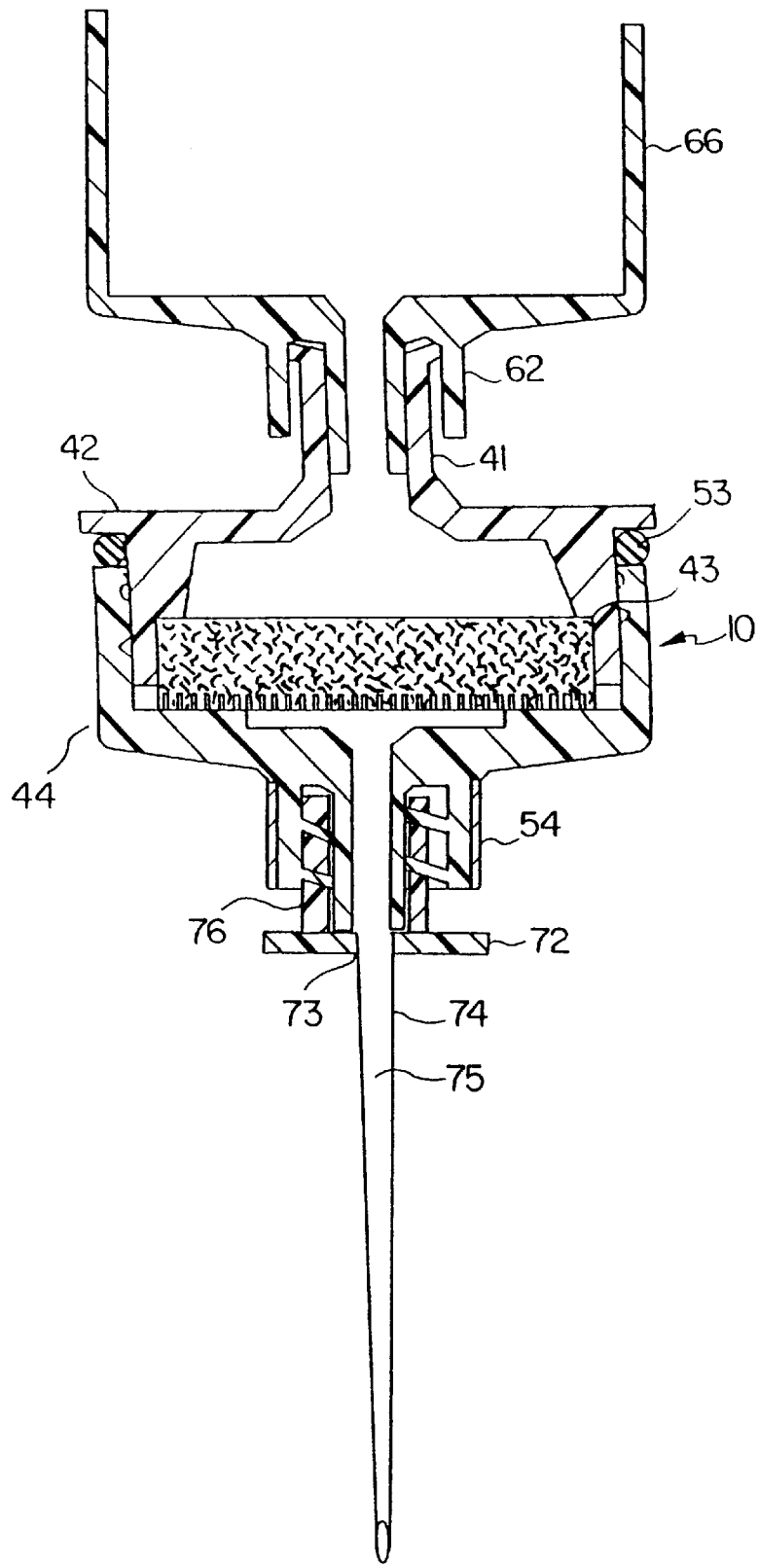
FIG. 9 is a schematic exploded cross sectional view of a needle member for aspiration biopsy and a syringe mounted on the cytology collection apparatus of FIGS. 1 and 2.

The first detachable portion 44 may be provided with a threaded luer lock 54 having a throughgoing bore 55 communicating with the chamber 50. The threaded luer lock 54 may be screwed onto nipple 28 of a collection cup 11 to remove liquid from the collection cup or alternatively attached to a needle assembly 70 as shown in FIG. 9. The needle assembly 70 is constructed with a support member 72 defining a throughgoing aperture 73 in which is mounted a fine aspiration needle 74 with a lumen 75. A threaded nipple member 76 is secured to the wall of the support member 72 thereby providing a means for the needle assembly 70 to be attached to the port 54 of the first detachable portion 44. Thus the needle assembly 70 can be used to aspirate biological fluid which is contained in the syringe or pump 66.

The present invention also includes a the method for transferring cells to a microscope slide. In contrast to currently available methods, the use of membrane filtration provides a method of depositing cells evenly over a slide with minimal overlap. This allows for clear observation and optimal diagnostic accuracy. As shown in FIG. 10, cells 60 from the collection site 45 on the surface of the polycarbonate membrane 46b may be placed on a glass slide 120 to transfer the cells, which then may be stained for cytologic determination. It is intended that the present invention should not be limited by the type of stain or detection protocol used.

Figure 12:
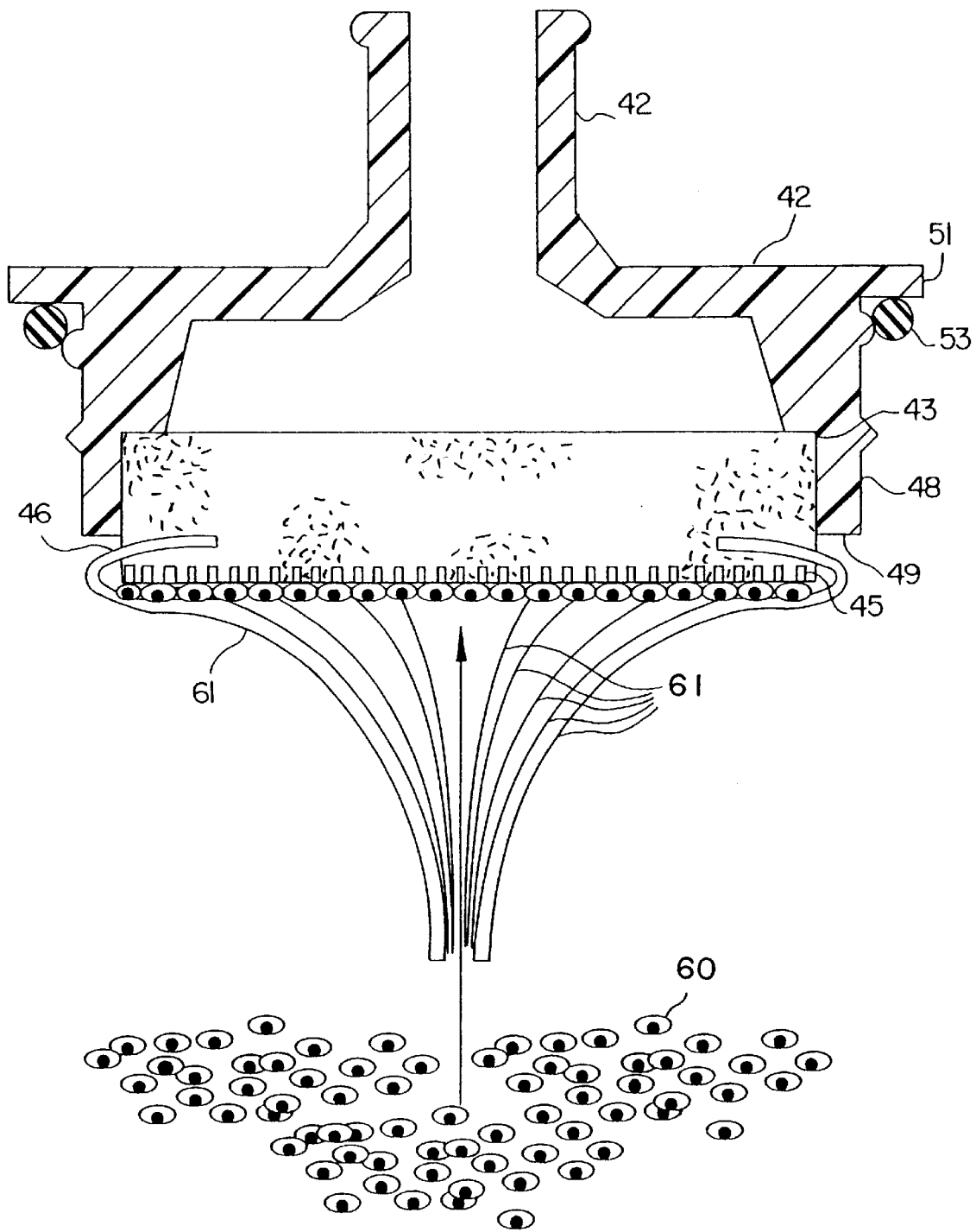
FIG. 12 is a schematic cross sectional view of the second detachable portion of the cytology collection apparatus of FIG. 8 showing fluid flowing through the side of the second porous medium and bypassing the first porous medium.
Figure 4:
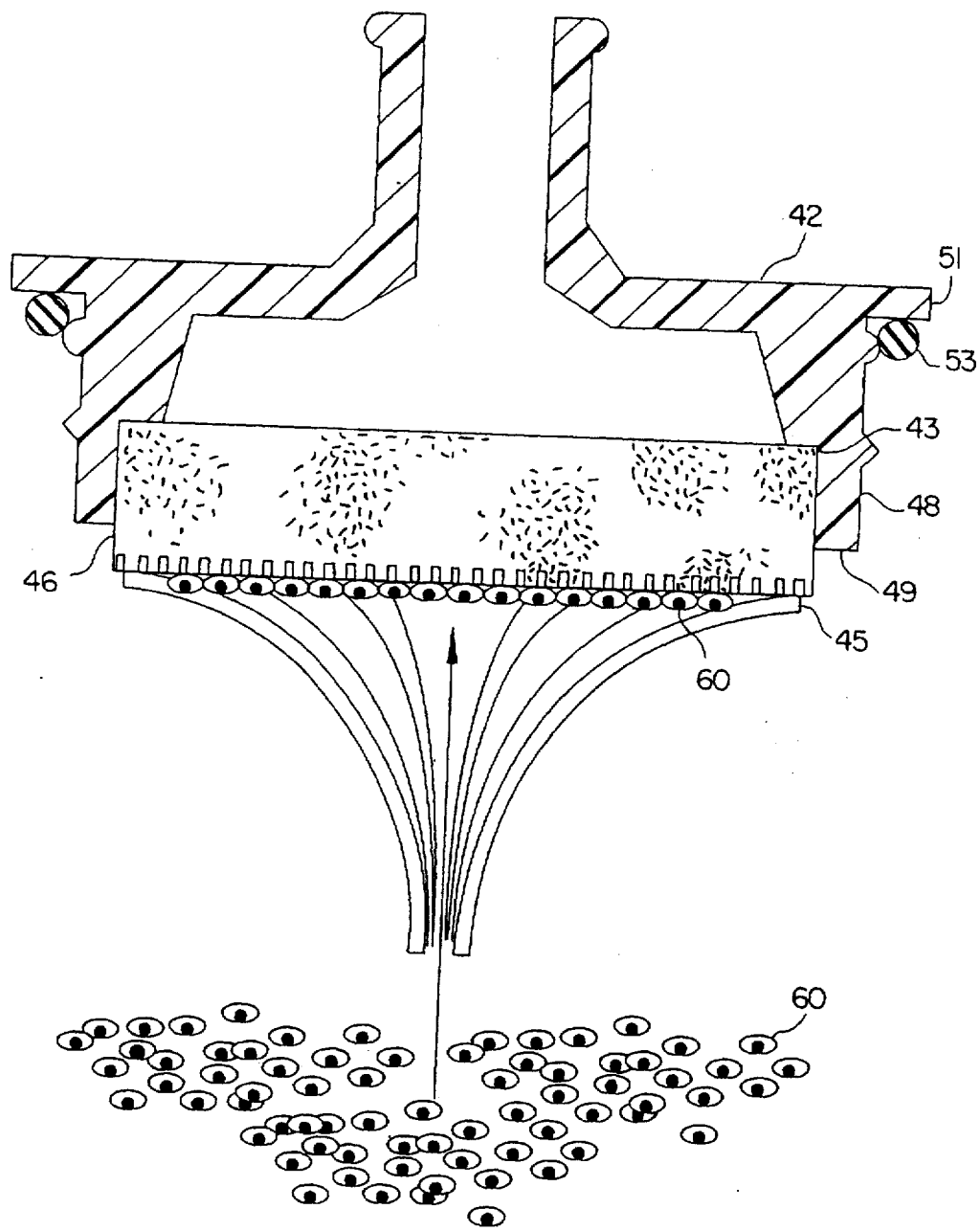
FIG. 4 is a cross sectional view of the second detachable portion of the cytology collection apparatus of FIGS. 1 and 2 as cells are collecting on the laminated filter mounted within the second detachable portion.
Figure 5:
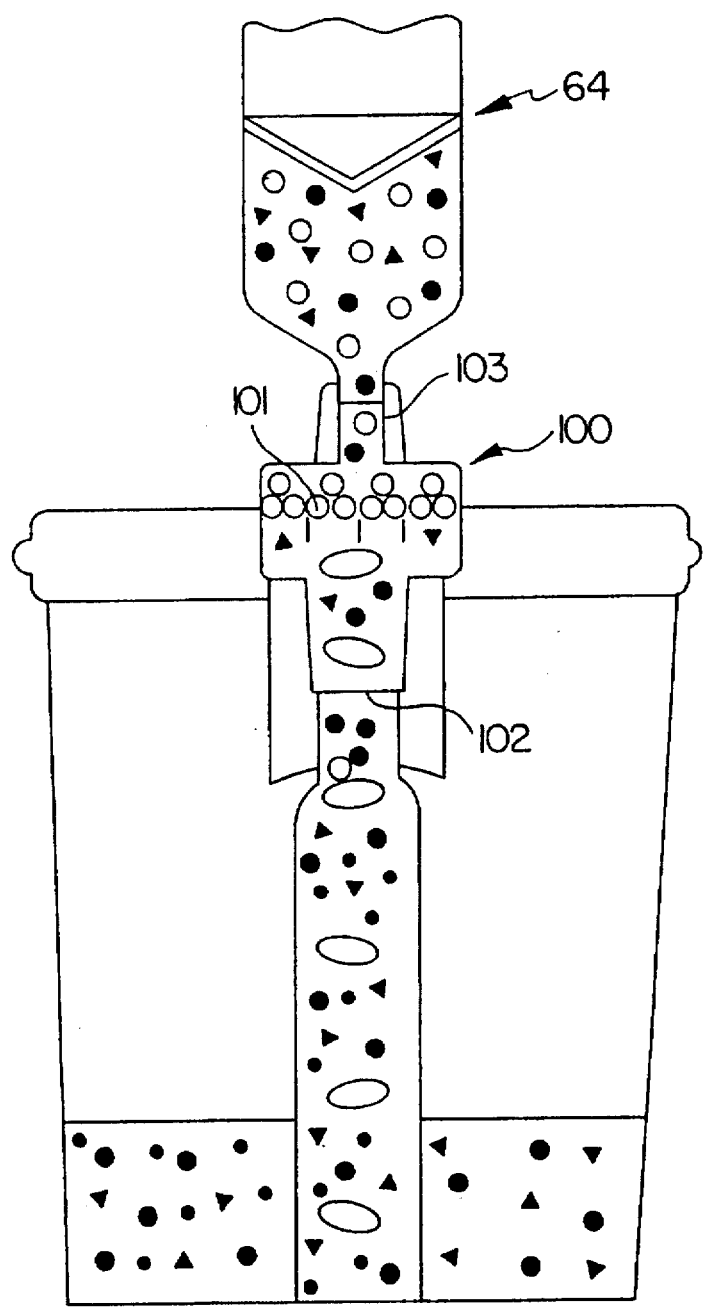
FIG. 5 is a cross sectional view of a debris removing device, detachably mounted on a collection cup, as fluid is aspirated through the device to remove debris and collect cells on a cell filter within the debris removing device.

When the biological fluid is pulled from the collection cup 11 through tube 30 and port 54 of the first detachable portion 44, fluid flows through porous membrane 46b and depth filter 46a as shown in FIG. 5, so that a monolayer of cells is formed on the surface 45 of the porous membrane 46b. Once the monolayer of cells is formed, fluid flow is reduced in the center of membrane 46b and increases towards the edges of the membrane 46b, as shown in FIG. 4. This may be due to the blockage of fluid flow by the collected cells as they form the monolayer on the surface 45 of membrane 46b. When the monolayer has mostly covered the surface 45 of membrane 46b, as shown in FIG. 12, the flow of fluid bypasses the membrane surface 45 and passes through the extended side area of the second porous medium 46a. Thus, the area of the second porous medium 46a extending beyond the end wall 49 of skirt 48 of the second detachable portion 42 acts as a vent (with low resistance to flow) which prevents the piling up of cells. The cytology collection apparatus 10 may then be disconnected from collection cup 11 and, optionally, from syringe 64. It may then be unscrewed into two parts and the second detachable portion 42 and accompanying cell coated membrane 46a may be placed on a slide 120, as shown in FIG. 10, so that a transfer of the membrane 46b with the monolayer on surface 45 occurs. The membrane 46b is then pressed on the slide using a tissue wipe allowing cells 60 to form a monolayer on the slide 120. The membrane 46b can be removed from the slide leaving the cells 60 on the slide. This allows a cytological examination to be performed on the cells by the practitioner without the interference of the pores in the membrane or delay due to processing requirements.

Figure 6:
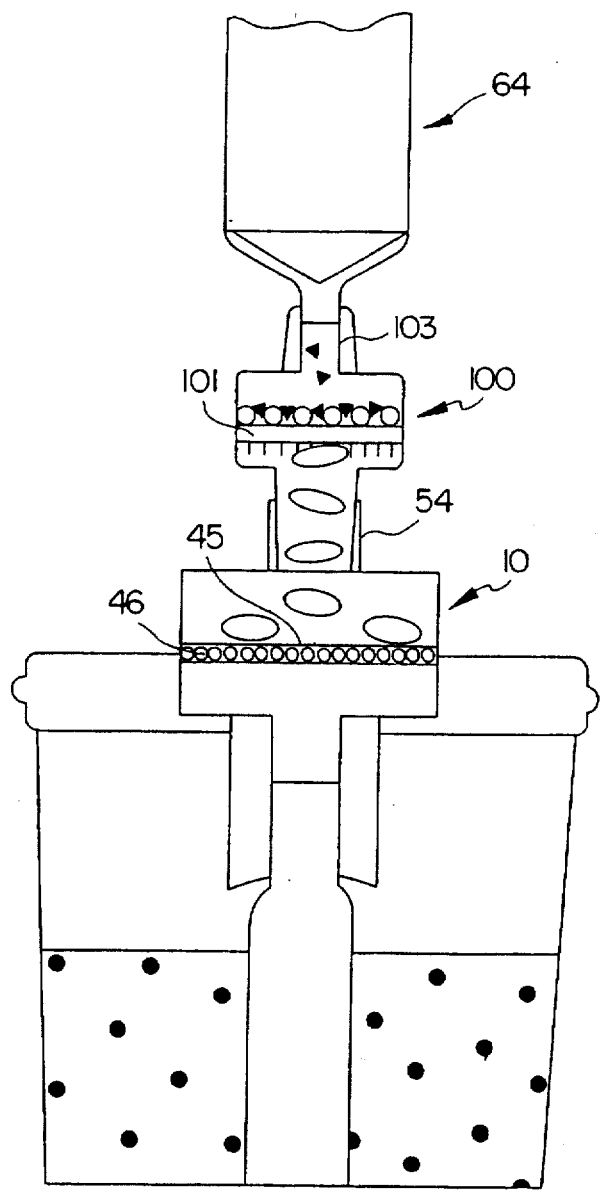
FIG. 6 is a cross sectional view of the debris removing device of FIG. 5, mounted on the cytology collection apparatus of FIG. 1, showing the expulsion of fluid through the debris removing device into the cytology collection apparatus where a cell monolayer is collected on the laminated membrane.

The cytology collection apparatus 10 described above may be used in combination with other suitable filtration or treatment devices. FIGS. 5 and 6 illustrate the use of a cytology collection apparatus 10 in combination with a debris filtering device 100. Any suitable debris filtration device 100, such as a debris Shuttle, may be used. The debris filtration device 100 preferably contains a cell filter 101, has an inlet 102 and outlet 103, and may be detachably connected to the cytology collection apparatus 10.

Referring to FIG. 5, a body fluid is first passed, preferably aspirated with a syringe, through the debris filtration device 100. As the body fluid passes through the debris filtration device 100, cells in the body fluid accumulate on the cell filter 101 mounted within the debris filtration device. The cell filter 101 should have pores large enough to permit debris to flow through while retaining the desired cells in the surface of the cell filter. The pore size of the cell filter 101 is preferably from about 3 microns to about 35 microns, more preferably 5 microns. Fluid is continually aspirated through the cell filter 101 until the flow is stopped by the accumulation of a cell mass on the filter.

After the flow of the body fluid ceases, the debris filtering device 100 may be connected to the first port 54 of the cytology collection apparatus 10. Fluid may be expelled through the debris filtering device 100 and the cytology collection apparatus 10, in a direction opposite that employed above. This results in the transfer of the cell mass, in the form of a monolayer, from the cell filter 101 of the debris filtering device 100 to collection site 45 of the porous arrangement 46 within the cell collection apparatus 10.

A treatment device may also be used in combination with the cytology collection apparatus 10. Any suitable diagnostic or detection assembly may be used in conjunction with the cytology collection apparatus 10. However, a preferable device is an apparatus for testing for the presence of cancer utilizing a sandwich assay. For example, the apparatus may comprise a housing including inlet and outlet ports defining a flow path between the inlet and the outlet; a filter positioned across the flow path; and substrate beads having a primary antibody bound to the surface thereof, the beads being contained within the outlet, as disclosed in U.S. Pat. No. 4,953,561.

The cytology collection apparatus 10 of the present invention also allows for isolation and collection of fresh cells and/or microorganisms from biological fluids to perform DNA probe and chromosomal analysis once the cells are hemolyzed by the proper buffer.

The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatic patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is very pleasing to the eye, possibly reducing eye strain.

Since cellular detail is dependent on fixation, it is preferred that cells be fixed immediately after being deposited on the slide. Too long a delay between preparation and fixation may expose the cells to drying, which may be detrimental to the cellular structure. Moreover, air drying artifacts can adversely affect the subsequent staining results. An exception is when the cells are stained with Wright-Giemsa, where air drying is used as the fixation step.

In an another embodiment of the present invention, the monolayer of cells may be fixed directly on the collection site. This may be carried out by first depositing a monolayer of cells on the collection site of the cytology collection apparatus as described above and subsequently passing a solution containing a fixative, such as alcohol or acetone, through the cytology collection apparatus.

Included within the scope of the present invention is the production of multiple specimens from a single patient sample. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the preparation does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

Figure 11:
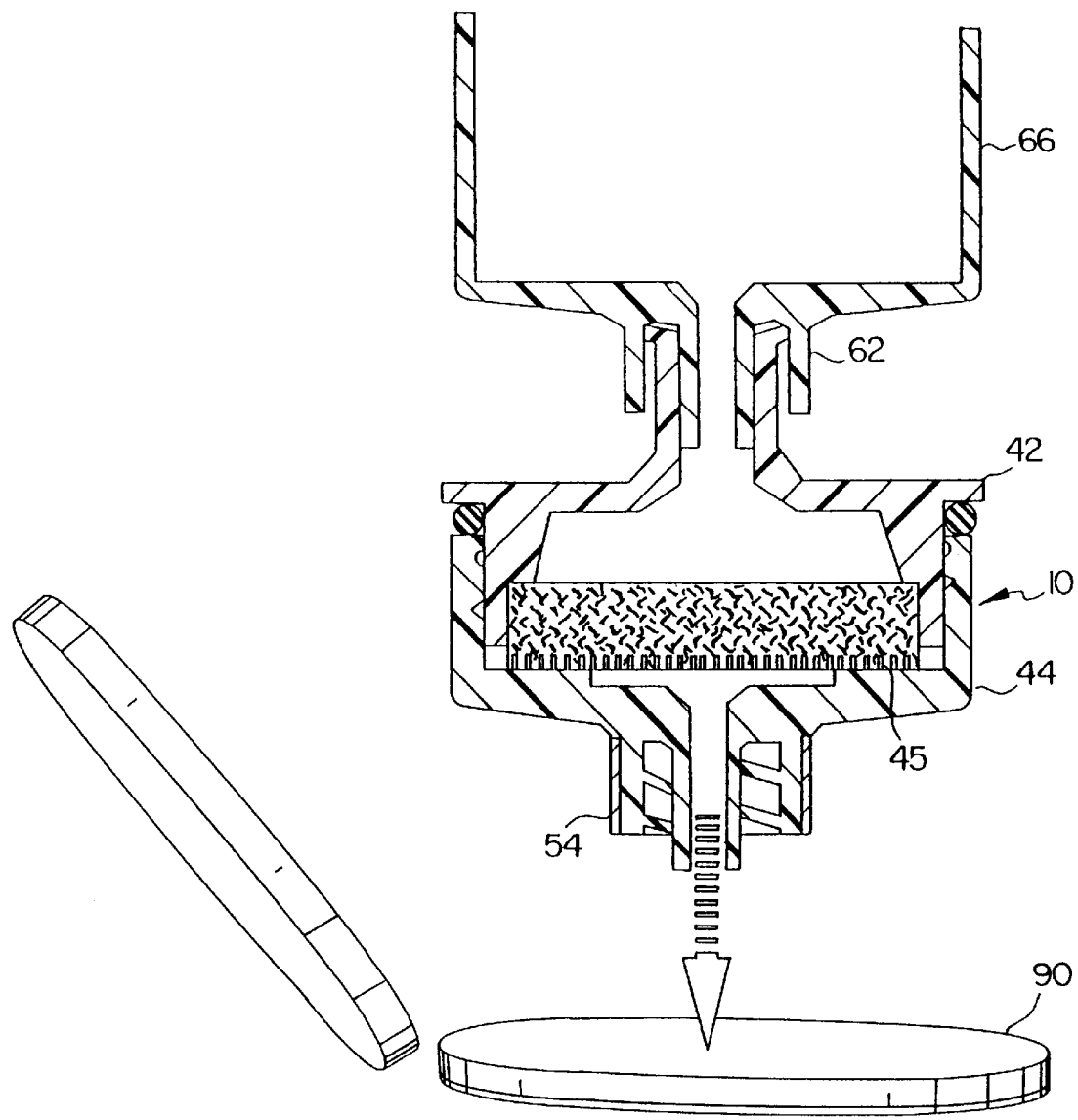
FIG. 11 is a schematic cross sectional view of a cytology collection apparatus, with the fluid collection cup removed, eluting a bacteriological sample into a microbiological culture tray.

Also, captured microorganisms can be cultured, as shown in FIG. 11, in culture medium such as a standard petri dish 90. After a monolayer of cells has been collected in the cytology collection apparatus 10, fluid may be passed through the collection site 45 towards first port 54, thereby transferring the microorganisms to the petri dish 90.

In bacteria testing, the membrane 45 can be used for culturing with a Qualture device (not shown) to determine the presence of specific bacteria colonies. The Qualture device is a plastic capsule containing a filter membrane and four nutrient pads of dehydrated, selective media.

The Qualture technique is more sensitive than the agar plate method and more rapid in determining a presumptive diagnosis. The device screens, isolates and presumptively diagnoses bacterial isolates in one step most often in 4–6 hours. Tests have demonstrated that recovery from fifty milliliters of fluid is excellent and sensitive.

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings. Therefore, the following claims are intended to cover any alternative embodiments, examples, modifications, or equivalents which may be included within the spirit and scope of the invention as defined by the claims.

I claim:

1. A cytology collection apparatus comprising:

first and second detachable portions defining a chamber;

first and second ports defining a flow path through the chamber; and a porous arrangement having a collection site adapted to collect cells positioned across the fluid flow path, the collection site communicating with the first port, wherein the porous arrangement is adapted to define a flow path having first and second branches, the first branch passing through the collection site and the second branch bypassing the collection site.

2. A cytology collection apparatus according to claim 1, wherein the porous arrangement includes a first porous medium capable of preventing the passage of cells therethrough and a second porous medium capable of removing particulate matter from a fluid.

3. A cytology collection apparatus according to claim 2, wherein the first porous medium is a porous membrane and the second porous medium is a depth filter.

4. A cytology collection apparatus according to claim 2, wherein the porous membrane is selected from the group consisting of a porous polycarbonate membrane, an unmodified nylon membrane, and a modified nylon membrane.

* * * * *

UNITED STATES PATENT AND TRADEMARK OFFICE
CERTIFICATE OF CORRECTION

PATENT NO.    : 6,106,483
DATED         : August 22, 2000
INVENTOR(S)   : Raouf A. Guirguis It is certified that error appears in the above-identified patent and that said Letters Patent is hereby corrected as shown below:

Figures 1-6 are deleted and replaced with the attached replacement Figures 1-6.

Signed and Sealed this

Twenty-sixth Day of March, 2002

Attest:

Attesting Officer

JAMES E. ROGAN
*Director of the United States Patent and Trademark Office*